US006120489A

United States Patent [19]
Johnson et al.

[11] Patent Number: 6,120,489
[45] Date of Patent: Sep. 19, 2000

[54] FLANGELESS SEAM FOR USE IN DISPOSABLE ARTICLES

[75] Inventors: Larry Kenneth Johnson; Stephen Joseph Lange, both of Cincinnati; David Michael Weirich, West Chester, all of Ohio

[73] Assignee: The Procter & Gamble Company, Cincinnati, Ohio

[21] Appl. No.: 08/855,651

[22] Filed: May 15, 1997

Related U.S. Application Data

[63] Continuation-in-part of application No. 08/541,377, Oct. 10, 1995, Pat. No. 5,662,638.

[51] Int. Cl.[7] ............................. A61F 13/15; A61F 13/20; A41D 27/24
[52] U.S. Cl. .......................... 604/386; 604/394; 604/396; 2/275; 2/400
[58] Field of Search .................................. 604/386, 392, 604/393, 394, 396, 387; 2/275, 400, 403, 406

[56] References Cited

U.S. PATENT DOCUMENTS

| | | | |
|---|---|---|---|
| 1,602,689 | 10/1926 | Lissner . | |
| 2,115,368 | 4/1938 | Lustberg | 2/275 |
| 2,298,522 | 10/1942 | Waters | 93/35 |
| 2,372,632 | 3/1945 | Webb | 2/275 |
| 2,494,905 | 1/1950 | Shumann | 93/35 |
| 4,205,679 | 6/1980 | Repke et al. | 604/394 |
| 4,610,681 | 9/1986 | Strohbeen et al. | 604/396 |
| 4,646,362 | 3/1987 | Heron et al. | 604/392 |
| 4,731,070 | 3/1988 | Koci | 604/385 R |
| 4,890,763 | 1/1990 | Curiel | 220/455 |
| 4,909,804 | 3/1990 | Douglas | 604/396 |
| 4,938,753 | 7/1990 | Van Gompel et al. | 604/385.2 |
| 4,938,757 | 7/1990 | Van Gompel et al. | 604/396 |
| 5,074,854 | 12/1991 | Davis | 604/396 |
| 5,185,052 | 2/1993 | Chappell et al. | 156/462 |
| 5,236,430 | 8/1993 | Bridges | 604/396 |
| 5,246,433 | 9/1993 | Hasse et al. | 604/396 |
| 5,491,846 | 2/1996 | Muller | 2/400 |
| 5,569,234 | 10/1996 | Buell et al. | 604/396 |
| 5,575,782 | 11/1996 | Hasse et al. | 604/385.1 |
| 5,618,366 | 4/1997 | Suckane | 604/396 |
| 5,624,420 | 4/1997 | Bridges et al. | 604/365 |
| 5,634,917 | 6/1997 | Fujioka et al. | 604/394 |
| 5,662,638 | 9/1997 | Johnson et al. | 664/387 |

FOREIGN PATENT DOCUMENTS

| | | |
|---|---|---|
| 0818188 | 1/1998 | European Pat. Off. . |
| 1047867 | 3/1986 | Japan ......................................... 2/275 |
| 2278993 | 12/1994 | United Kingdom . |

*Primary Examiner*—Mark O. Polutta
*Attorney, Agent, or Firm*—David M. Weirich; Steven W. Miller; Jacobus C. Rasser

[57] ABSTRACT

A flangeless seam especially useful in disposable articles, such as training pants, incontinence articles and the like. The first member preferably has a first proximal portion and a first distal portion. The first distal portion is preferably folded upon at least a portion of the first proximal portion to provide a common interface between the first distal portion and the first proximal portion when the seam is in the seaming configuration. The first proximal portion preferably has a first melting point and the first distal portion preferably has a second melting point which is relatively lower than the first melting point. The seam also includes a second member preferably having a second proximal portion and a second distal portion. The second member preferably has a third melting point which is lower than the first melting point. The first distal portion and the second distal portion are joined to one another at a temperature which is relatively lower than the first melting point of the first proximal portion and at least a part of the first proximal portion is not joined to at least a part of the first distal portion such that the unjoined parts of the first proximal portion and the first distal portion may be separated to provide the seam in its open configuration.

20 Claims, 3 Drawing Sheets

FLANGELESS SEAM FOR USE IN DISPOSABLE ARTICLES

This application is a continuation-in-part of application Ser. No. 08/541,377, filed on Oct. 10, 1995, now U.S. Pat. No. 5,662,638.

FIELD OF THE INVENTION

The present invention relates to flangeless seams especially preferred for use in disposable, pant-like articles having at least one fixed side comprising a seam. Examples of such disposable articles include training pants, pull-on diapers or adult incontinence articles, disposable underwear for children (e.g., toddlers) or adults, and disposable panties which may be used with catamenial devices such as tampons or sanitary napkins.

BACKGROUND OF THE INVENTION

Infants and other incontinent individuals wear disposable absorbent articles to receive and contain urine and other bodily exudates. Absorbent articles having fixed sides have been popular for use in adult incontinence articles and children's toilet-training articles because it is desirable to have an absorbent article which is very garment-like in appearance and feel. (As used herein, "articles having fixed sides" refer to disposable articles such as adult incontinence briefs and training pants which are provided to the consumer in a pant-like configuration. Thus, the articles generally have the front and rear portions joined together to form a waist hoop and leg openings. This is unlike conventional diapers which are provided to the consumer with the front and rear portions unjoined.) For adults, the garment-like appearance and feel can help reduce any embarrassment associated with the use of incontinence articles. For children, especially in their toilet training stage, the garment-like feel and appearance can help the child distinguish the article, such as training pants, from a diaper and can help the child adjust to cloth undergarments.

With regard to disposable articles such as adult incontinence briefs and training pants, consumers are very conscious about the fit, containment characteristics and the overall appearance of the articles. One improvement that has become popular with consumers has been the addition of stretch or elasticity throughout different portions of the articles. One example of a commercially available disposable training pant is disclosed in U.S. Pat. No. 5,246,433 entitled "Elasticized Disposable Training Pant and Method of Making the Same", issued to Hasse et al. on Sep. 21, 1993, which is hereby incorporated by reference herein.

Despite the improvements made to disposable articles having fixed sides, such articles generally include seams for joining the front and rear portions. The seams are often constructed by positioning the lateral edges of the front and rear portions of the article in a face-to-face relationship with one another and then gluing, sewing, heat sealing or ultrasonically sealing the edges to form flanges or fin seams. Flanges or fin seams can be unsightly if located on the outwardly facing surface of the article or irritating to the wearer if located on the inward surface. Thus, attempts have been made to reduce the outwardly or inwardly extending portions of the flanges of fin seams. However, doing so may reduce the strength of the bond between the front and rear portions of the article which may allow the seam to fail during use.

Another important aspect of a disposable article is the cost of the article. Because the article is intended to be discarded, generally after a single use, consumers are very conscious of the cost of the article. Thus, it would be advantageous to be able to provide a seam that can be constructed economically on machinery that is very similar to that already in place. Further, it would be advantageous to reduce the amount of material that is needed to produce a satisfactory seam or that is wasted in attempting to make the seam more preferable to the consumer.

Therefore, it is an object of the present invention to provide flangeless seams especially suited for use in disposable articles, such as disposable training pants, adult incontinence briefs and the like which are discrete, strong and economical to manufacture.

It is another object of the present invention to provide flangeless side seams which can be produced more quickly and easily than the sewn seams of the prior art and which provide a more garment-like appearance and are less irritating than the heat-sealed, adhesively bonded or ultrasonically sealed seams of the prior art.

It is yet another object of the present invention to provide flangeless side seams which reduces the amount of material needed to produce the seam as well as the material waste associated with providing a seam that is acceptable to the consumer.

It is a further object of the present invention to provide a disposable article, such as disposable training pants, having flangeless seams.

SUMMARY OF THE INVENTION

According to the present invention, a flangeless seam especially useful in disposable articles, such as training pants, incontinence articles and the like is provided. The flangeless seam preferably comprises a first member and a second member, wherein at least a portion of the second member overlaps at least a portion of the first member.

The first member preferably has a first proximal portion and a first distal portion. The first distal portion is preferably folded upon at least a portion of the first proximal portion to provide a common interface between the first distal portion and the first proximal portion when the seam is in the seaming configuration. The first proximal portion preferably has a first melting point and the first distal portion preferably has a second melting point which is relatively lower than the first melting point. The seam also includes a second member preferably having a second proximal portion and a second distal portion. The second member preferably has a third melting point which is lower than the first melting point. The first distal portion and the second distal portion are joined to one another at a temperature which is relatively lower than the first melting point of the first proximal portion and at least a part of the first proximal portion is not joined to at least a part of the first distal portion such that the unjoined parts of the first proximal portion and the first distal portion may be separated to provide the seam in its open configuration.

While the flangeless seams of the present invention may be used in any disposable article, a preferred disposable article comprises an elasticized waistband, elasticized leg cuffs and an absorbent assembly comprising a backsheet, topsheet, and absorbent core.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIGS. 5A–G are schematic views of a parts of one method for making the seams of the present invention;

DETAILED DESCRIPTION OF THE INVENTION

Figure 1:
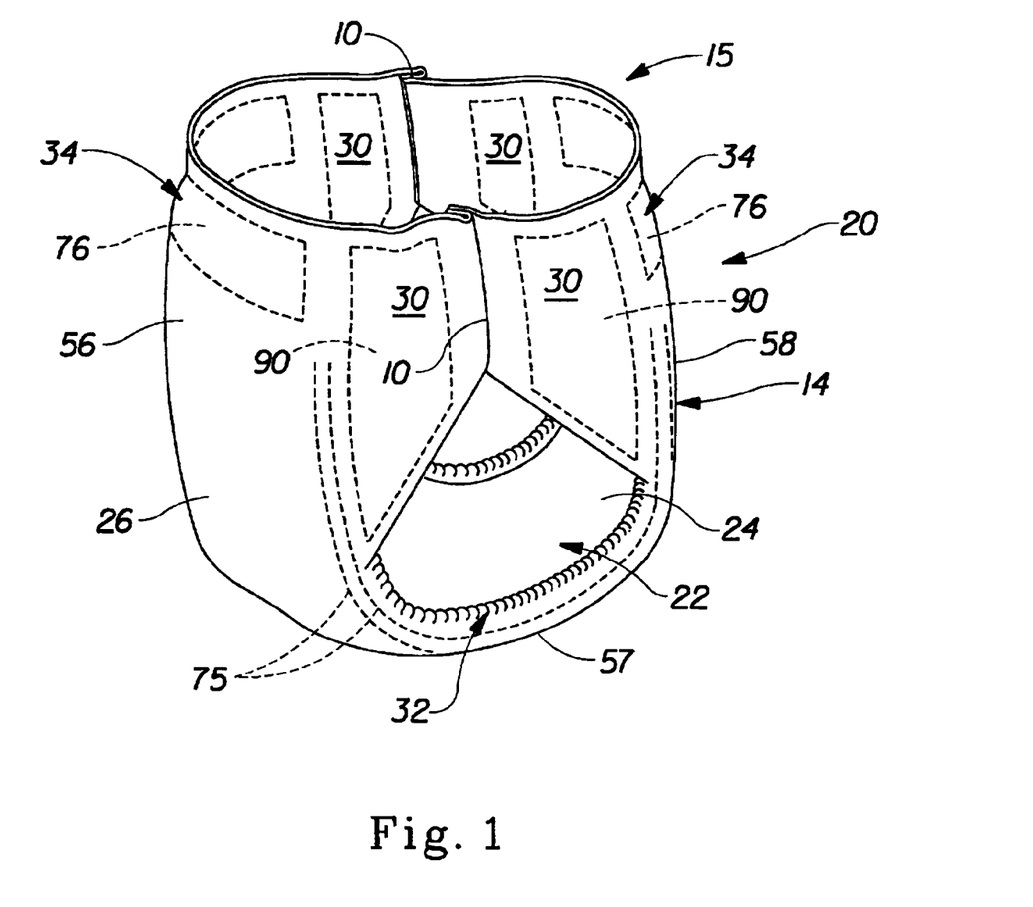
FIG. 1 is a perspective view of a disposal training pant embodiment of the present invention in a typical in-use configuration as it would be applied to a wearer.

Referring to the drawings, it will be noted that FIG. 1 is a perspective view of a disposable garment 15. A disposable garment is one which is intended to be discarded after it is used (i.e., it is not intended to be laundered or otherwise restored or reused). The disposable garment 15 may be provided with an absorbent assembly which is placed in close proximity to the body of the wearer to absorb and contain the various exudates discharged from the body. A preferred embodiment of the disposable garment 15 of the present invention, disposable training pants 20, is shown in FIG. 1. Examples of other suitable training pants, as well as preferred components and alternative embodiments, in which the flangeless seams of the present invention may be used can be found in U.S. Pat. No. 5,236,430 entitled "Disposable Training Pant Having Fusion-Slit Side Seams", issued to Russell P. Bridges on Aug. 17, 1993, U.S. Pat. No. 5,246,433 entitled "Elasticized Disposable Training Pant and Method of Making the Same", issued to Hasse et al. on Sep. 21, 1993; and U.S. Pat. No. 5,622,589 entitled "Method Of Making A Flangeless Seam For Use In Disposable Articles", issued to Johnson et al. on Apr. 22, 1997. The specification, claims and drawings of each of these patents are hereby incorporated by reference herein.

The training pants 20 of FIG. 1, preferably comprise a chassis 14, an absorbent assembly 22, and at least one flangeless seam 10. (As used herein the term "flangeless seam" refers to a seam which extends from the disposable training pants 20 about ⅛ inch or less. Preferably the flangeless seam will extend from the article about ¹⁄₁₆ inch or less, and more preferably about ¹⁄₃₂ inch or less.) The chassis 14 of the present invention preferably has a symmetric, modified hour-glass shape. The chassis 14 preferably comprises a front portion 56, a rear portion 58, a crotch portion 57. The chassis 14 preferably further comprises elasticized leg cuffs 32, an elasticized waistband 34, elasticized side panels 30 and longitudinal side regions 88 (shown in FIG. 2). The longitudinal side regions 88 preferably comprise a polymeric material to facilitate the seaming process which is described in greater detail below.

Figure 2:
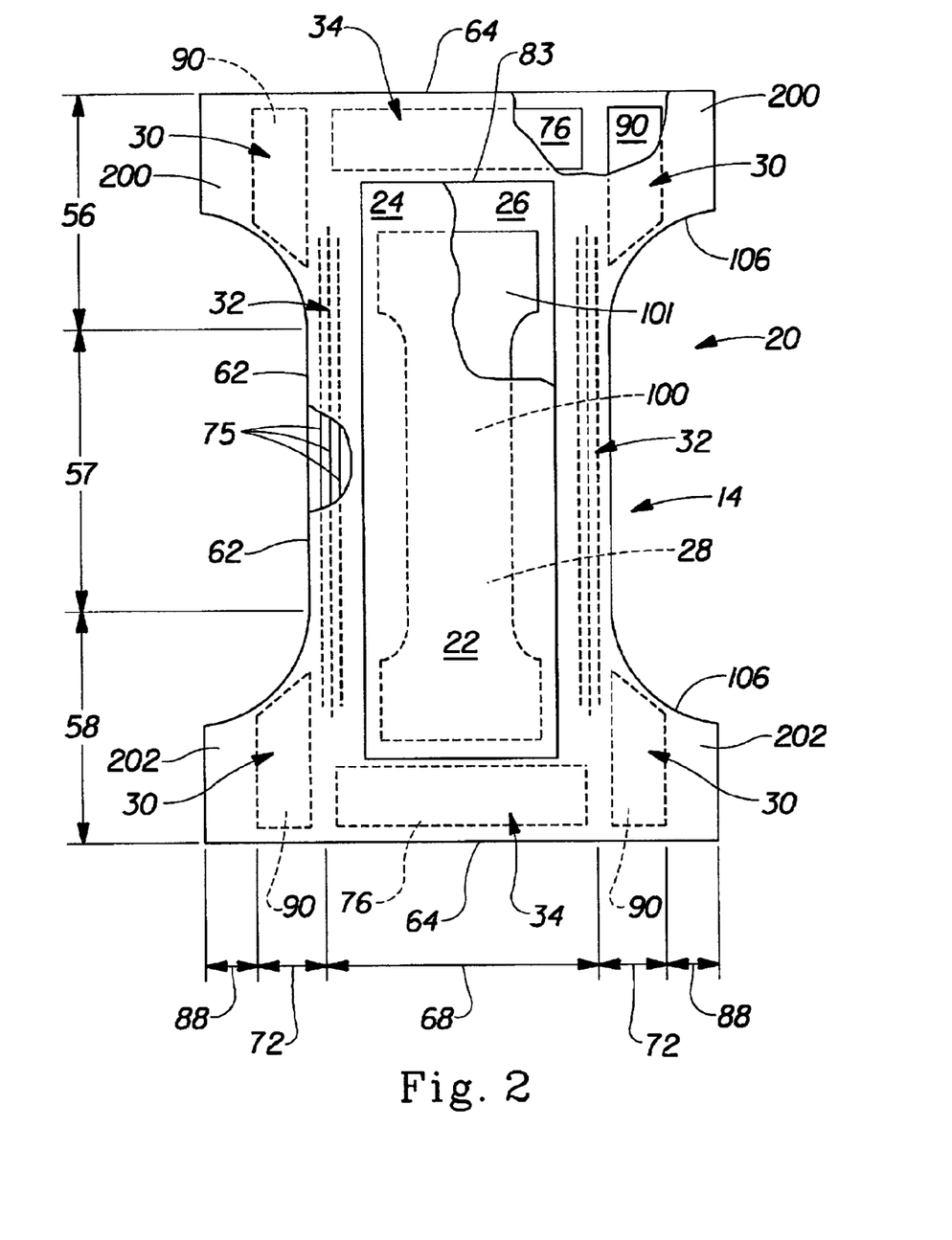
FIG. 2 is a plan view of the chassis of a training pant embodiment of the present invention having portions cut away to reveal the underlying structure, the surface which will form the outer surface of the disposable article facing away from the viewer.

FIG. 2 is a partially cut-away perspective view of the disposable garment 20 of FIG. 1, prior to the front portion 56 and rear portion 58 of the chassis 14 being joined together. (As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.)

The chassis 14 of the present invention preferably has a symmetric, modified hour-glass shape. The chassis 14 will have at least a front portion 56, a rear portion 58, a crotch portion 57, and longitudinal side regions 88, and will comprise a polymeric material in at least the longitudinal side regions 88 to facilitate the seaming process which will be described in greater detail herein below. Further, as shown in FIG. 2, a preferred embodiment of the chassis 14 will comprise an absorbent assembly 22. The absorbent assembly 22 of the disposable training pants 20 may be integral with the training pants 20 or may be an insert, i.e. an element formed separately from the chassis and inserted therein.

As shown in FIG. 2, the absorbent assembly 22 of the disposable training pants 20 preferably comprises at least an absorbent core 28 and an outer covering layer comprising a topsheet 24 and a backsheet 26. The absorbent core 28 preferably has a garment surface 100 and a body surface 101. The absorbent core 28 may be any absorbent means which is generally compressible, conformable, nonirritating to the wearer's skin, and capable of absorbing and retaining liquids such as urine and other certain body exudates.

The absorbent core 28 may be manufactured in a wide variety of sized and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the disposable garment 20. Further, the size and absorbent capacity of the absorbent core 28 may be varied to accommodate wearers ranging from infants through adults. An exemplary absorbent structure for use as the absorbent core 28 of the present invention are described in U.S. Pat. No. 4,610,678 entitled "High-Density Absorbent Structures" issued to Weisman and Goldman on Sep. 9, 1986; U.S. Pat. No. 4,673,402 entitled "Absorbent Articles With Dual-Layered Cores" issued to Weisman, Houghton, and Gellert on Jun. 16, 1987; and U.S. Pat. No. 4,888,231 entitled "Absorbent Core Having A Dusting Layer" issued to Angstadt on Dec. 19, 1989. Each of these references are incorporated herein by reference.

The backsheet 26 is positioned adjacent the garment surface 100 of the absorbent core 28 and is preferably joined thereto by attachment means such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combination of these attachment means as are known in the art.

The backsheet 26 is impervious to liquids (e.g. urine) and is preferably manufactured from a thin plastic film, or nonwoven material, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the disposable training pants 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a film having a thickness of from about 0.012 mm (0.5 mil) to about 0.051 mm (2.0 mils).

The size of the backsheet 26 is dictated by the size of the absorbent core 28 and the exact disposable garment design selected. In one embodiment, the backsheet 26 will wrap around at least the absorbent core and possibly over the edge portions of the topsheet 24 in at least the crotch portion 57, so that the elasticized leg cuff 32 will be free from any backsheet material, and thus, are not inhibited by the backsheet material. Alternatively, the topsheet 24 may wrap around the core and under the edge portions of the backsheet 26 in at least the crotch portion 57, or the topsheet 24 and backsheet 26 may be "side-notched" in the crotch portion 57 so that the elasticized leg cuffs 32 are not inhibited by the backsheet material.

The topsheet 24 is positioned adjacent the body surface 101 of the absorbent core 28 and is preferably joined thereto and to the backsheet 26 by attachment means such as those well known in the art. Suitable attachment means are described with respect to joining the backsheet 26 to the absorbent core 28. In one preferred embodiment of the present invention, the topsheet 24 and the backsheet 26 are joined directly to each other in the areas extending beyond the absorbent core 28 and are indirectly joined together by directly joining them to the absorbent core 28 by the attachment means.

The topsheet 24 is compliant, soft feeling, and nonirritating to the wearer's skin. Further, the topsheet 24 is liquid pervious permitting liquids (e.g. urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. In one embodiment, the topsheet 24 is made of hydrophilic material comprising about 20% to 30% rayon so as to feel wet and signal a discharge of urine to a toilet training child. A suitable topsheet is manufactured by Fiberweb North America and available as 80/20 polypropylene/rayon carded thermally bonded nonwoven.

In a preferred embodiment of the present invention, at least a portion of the topsheet 24 and the backsheet 26 will be subjected to mechanical stretching in order to provide a "zero strain" stretch laminate that forms the elasticized side panels 30. Thus, the topsheet 24 and the backsheet 26 are preferably elongatable, most preferably drawable, but not necessarily elastomeric, so that they will, upon mechanical stretching, be at least to a degree permanently elongated such that they will not fully return to their original undistorted configuration. In preferred embodiments, the topsheet 24 and the backsheet 26 can be subjected to mechanical stretching without undue rupturing or tearing. Thus, it is preferred that the topsheet 24 and the backsheet 26 have a low cross-machine direction (lateral direction) yield strength.

Examples of such "zero strain" stretch laminates are disclosed in U.S. Pat. No. 2,075,189 issued to Galligan, et al. on Mar. 30, 1937; U.S. Pat. No. 3,025,199 issued to Harwood on Mar. 13, 1962; U.S. Pat. No. 4,107,364 issued to Sisson on Aug. 15, 1978; U.S. Pat. No. 4,209,563 issued to Sisson on Jun. 24, 1980; U.S. Pat. No. 4,834,741 issued to Sabee on May 30, 1989; and U.S. Pat. No. 5,151,092 issued to Buell et al., on Sep. 29, 1992. All of the above referenced patents are hereby incorporated by reference.

Alternatively, the topsheet and backsheet 24 and 26, portions thereof or any other element of the disposable article 20 may comprise a structural elastic-like film (SELF) web. A structural elastic-like film web is an extensible material that exhibits an elastic-like behavior in the direction of elongation without the use of added elastic materials. SELF webs suitable for the present invention are more completely described in U.S. Pat. No. 5,554,145 entitled "Absorbent Article with Multiple Zone Structural Elastic-Like Film Web Extensible Waist Feature" issued to Donald C. Roe, et al. on Sep. 10, 1996, and U.S. Pat. No. 5,518,801 entitled "Web Materials Exhibiting Elastic-Like Behavior" issued to Chappell, et al. on May 21, 1996, both of which are incorporated herein by reference.

The disposable training pant 20 preferably further comprise elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractible Side Portions For a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edgeleakage-guard gutters configured to contain free liquids within the garment. Each of these patents are incorporated herein by reference. While each elasticized leg cuff 32 may be configured so as to be similar to any of the leg bands, side flaps, barrier cuffs, or elastic cuffs described above, it is preferred that each elasticized leg cuff 32 comprise one or more elastic strands 75.

The disposable training pant 20 may also comprise an elasticized waistband 34 disposed adjacent the end edge 64 of the disposable training pants 20 in at least the rear portion 58, the front portion 56 or both the front portion 56 and the rear portion 58. (As used herein, the term "disposed" is used to mean that an element(s) of the disposable garment is formed (joined and positioned) in a particular place or position as an unitary structure with other elements of the disposable garment or as a separate element joined to another element of the disposable garment.)

The waistband of the disposable training pants 20 is that portion which is intended to be placed adjacent the wearers waist. The elasticized waistband 34 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. Thus, the waistband is generally that portion of the disposable training pants 20 extending from the end edge 64 of the disposable training pants 20 to at least the waist edge 83 of the absorbent core 28. While the elasticized waistband 34 can comprise a separate element affixed to the chassis 14 of the disposable training pants 20, the waistband is preferably an extension of other elements of the disposable training pants 20 such as the topsheet 24, the backsheet 26, or any combination of these elements and an elastomeric material joined thereto.

The elasticized waistband 34 may be constructed in a number of different configurations including those described herein with regard to the elasticized side panels 30. In a preferred embodiment of the present invention shown in FIG. 2, the elasticized waistband 34 comprises an elastic waistband member 76 interposed between the topsheet 24 and the backsheet 26 and operatively associated with either or both the topsheet 24 or the backsheet 26 to gather the front portion 56 and rear portion 58 of the disposable training pants 20. An example of such an elasticized waistband for use herein is the elasticized waistband disclosed in U.S. Pat. No. 4,515,595 entitled "Disposable Diapers With Elastically Contractible Waistbands", which issued to Kievit and Osterhage on May 7, 1985, and which patent is incorporated herein by reference.

Any suitable elastomeric material as known in the art may be used as the elastic waistband member 76 of the present invention. Examples of suitable elastomeric materials include elastomeric films, elastomeric foams such as polyurethane foams or crosslinked natural rubber foams; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates as described hereinbefore or mechanically stretched pretensioned stretch laminates and elastic strands made from rubber, LYCRA, or other materials. In a preferred embodiment, the elastic waistband member 76 comprises a heat shrinkable elastomeric film.

In an alternative embodiment, the elasticized waistbands 34 and the elasticized side panels 30 can be formed by securing a single piece of elastomeric material to the disposable training pants 20 in both the side panels 72 and the central region 68 of the rear portion 58 and securing a single piece of elastomeric material to the disposable training pants 20 in both the side panels 72 and central region 68 of the front portion 56. Thus, the elasticized waistband 34 and the elasticized side panels 30 can be formed from the same piece of material to form a unitary structure.

In a preferred embodiment, the disposable garment also comprises elasticized side panels 30 disposed in the front portion 56 and rear portion 58. The elasticized side panels 30 provide an elastically extensible feature that provides a more comfortable and contouring fit by initially conformably fitting the disposable garment to the wearer and sustaining this fit throughout the time of wear well past when the disposable garment has been loaded with exudates since the elasticized side panels allow the sides of the disposable garment to expand and contract. While the disposable training pants 20 of the present invention preferably has the elasticized side panels 30 disposed in both the front portion 56 and rear portion 58; alternatively, the disposable training pants 20 may be provided with elasticized side panels 30 disposed in the front portion 56 only or in the rear portion 58 only.

The elasticized side panels 30 of the disposable training pants 20 may be constructed in a number of configurations. The elasticized side panels 30 of the present invention may be unitary or integral with the chassis 14 or may comprise a separate elastically extensible material or laminate joined to the chassis 14. As shown in FIGS. 1 and 2, each elasticized side panel 30 preferably comprises an elastic side panel member 90 operatively associated therewith. Examples of a disposable articles with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and U.S. Pat. No. 5,246,433 issued to Hasse et al., on Sep. 21, 1993. Each of these patents is hereby incorporated by reference herein.

As shown in FIG. 2, each side panel 72 preferably may comprise a portion of the chassis 14 that extends laterally outwardly from and along the central region 68 of the chassis 14 to the longitudinal side region 88 of the chassis 14. The side panel 72 generally extends longitudinally from the end edge 64 of the chassis 14 to the portions of the longitudinal edge 62 of the chassis 14 that forms the leg opening (this segment of the longitudinal edge 62 being designated as leg edge 106). In a preferred embodiment of the present invention, each side panel 72 is formed by the portions of the topsheet 24 and the backsheet 26 that extend beyond the central region 68 of the chassis 14.

Preferably, the chassis 14 comprises at least one longitudinal side region 88 having a first member 200 and a second member 202. As shown in FIG. 2, the chassis 14 more preferably comprises a pair of opposing longitudinal side regions 88, each of which each comprise a first member 200 and a second member 202. (Although the first members 200 are shown in FIG. 2 to be disposed in the front portion 56 and the second members 202 are shown to be disposed in the rear portion 58, embodiments are contemplated wherein the first members 200 are disposed in the rear portion 58 and the second members 202 are disposed in the front portion 56.) In preferred embodiments of the present invention, at least one pair of the first and second members 200 and 202 are joined by means of the flangeless seams described below to form a closure that joins at least a part of the front portion 56 of the chassis 14 with at least a part of the rear portion 58 of the chassis 14. More preferably, both pairs of first and second members 200 and 202 are joined by means of the flangeless seams to form a disposable pant having a waist hoop 40 and a pair of leg openings 44. (One embodiment is shown in FIG. 8.)

The first and second members 200 and 202 may be separate members joined to the longitudinal side regions 88 or may be integral with the longitudinal side regions 88. (As used herein, the term "integral" refers to elements that are joined to one another in such a way that the elements are neither divided nor discontinuous with the other elements.) If the first and second members 200 and 202 are joined with the chassis 14, any suitable means for joining known in the art may be used. In preferred embodiments, the first and second members 200 and 202 are extensions of the topsheet 24, the backsheet 26, both the topsheet 24 and the backsheet 26 or any other element of the disposable article that may be suitable for joining to form a flangeless seam. In one embodiment, at least a portion of the first member 200 in the second member may be coextruded with the topsheet 24 or the backsheet 26.

The first member 200 and the second member 202 may comprise any material known in the art that is suitable for use in disposable articles such as training pants 20 which may be joined together to form the flangeless seam 10 of the present invention. Preferably, at least a portion of the first member 200 or the second member 202 has a higher melting point than the rest of the material to be joined in the seam area 250. The portion of the first member 200 or second member 202 with the higher melting point will not melt when the rest of the layers of the seam are joined. This is what provides the seam 10 the ability to open to a flat or flangeless seam. In one preferred embodiment, at least a portion of the first member 200 and at least a portion of the second member 202 will include polypropylene. In the same embodiment, at least a portion of the first member 200 will include polyester with a relatively higher melting point than the polypropylene such that part of the first member 200 will not be joined to the second member 202. In an alternative embodiment, the first and second members 200 and 202 may include polyethylene and at least a part of the first portion will include a polypropylene. In such embodiments, the polypropylene will generally have a relatively higher melting point than the polyethylene.

The materials making up the first member 200 and the second member 202 may include polymeric fibers, films, and other suitable materials including woven webs, non-woven webs, apertured films, scrims, foams or combinations of these or other materials known in the art. Examples of suitable materials include Clopay 1401 polyethylene film available from the Clopay Corporation of Cincinnati, Ohio, and FS2 or Plus polyethylene films available from Tredegar Film Products, Inc., of Terre Haute, Ind., Mantel 442 polypropylene nonwoven resin and RMS 66295 carded nonwoven from Veratec, Nonwoven Group of Walpole, Mass.

The Flangeless Seam

Figure 3:
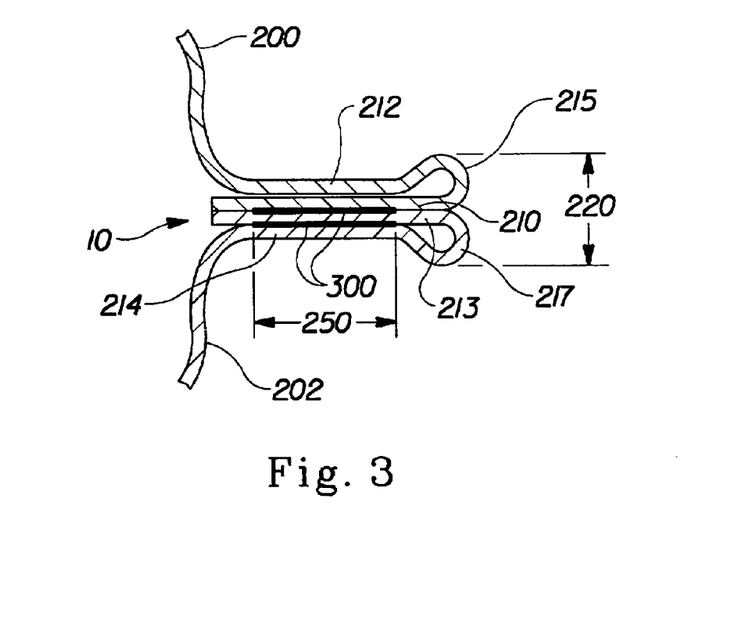
FIG. 3 is an enlarged cross-sectional view of one embodiment of the seam area in the configuration in which the seam is fixed.
Figure 4:
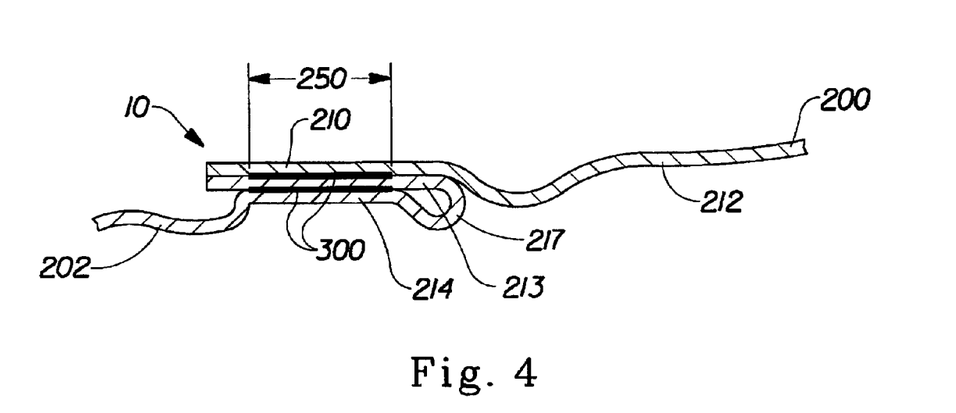
FIG. 4 is an enlarged cross-sectional view of the seam area shown in FIG. 3 in an open configuration.

One embodiment of the flangeless seam 10 of the present invention is shown in FIGS. 3 and 4. The flangeless seam 10 preferably has an open configuration and a seaming configuration. As used herein, the term "seaming configuration" refers to a configuration in which the elements of the seam 10 may be positioned with regard to each other and joined to form the seam 10. (FIG. 3) The term "open configuration" refers to the configuration of the elements comprised in the seam 10 after they have been opened or placed in a configuration in which the seam 10 is likely to be used, such as in a diaper that has been placed on a wearer. (FIG. 4) When the flangeless seam 10 is in the seaming configuration (FIG. 3), a laminate 220 is formed. The laminate 220 preferably comprises at least a part of the first member 200 and at least a part of the second member 202.

The first distal portion 210 is preferably foldable upon at least a portion of the first proximal portion 212 so as to provide a common interface between the first distal portion 210 and the first proximal portion 212. The flangeless seam 10 preferably further comprises a second member 202 having a second proximal portion 214 and a second distal portion 213 separated by a fold 217. In an alternative embodiment, the second member 202 does not include a fold. The first distal portion 210 and the second distal portion 213 are preferably joinable to one another as are the second distal portion 213 and the second proximal portion 214.

The lengths of the proximal portions 212 and 214 and the distal portions 210 and 213 are not critical, and each may comprise any number of layers and/or folds. In fact, it is recognized that one way to increase the strength of the finished seam is to provide more material in the seam area 250. This is especially relevant when the seam is joined by means of heat, pressure, heat and pressure, or ultrasonic bonding and when at least a portion of the bond is made from the material in the seam area 250.

The flangeless seam 10 preferably further comprises bond(s) 300. The bond(s) 300 preferably join at least a part of the first distal portion 210 with at least a part of the second distal portion 213. Further, a bond 300 may join at least a portion of the second proximal portion 214 to a portion of the second distal portion 213, as shown in FIG. 3. However, there is preferably no bond between at least a part of the first proximal portion 212 and the first distal portion 210 as shown in FIGS. 3–4. At least a portion of the first proximal portion 212, however, is not bonded to the first distal portion 210. Thus, the unjoined parts of the first proximal portion 212 and the first distal portion 210 may be separated to provide the flangeless seam 10 in its open configuration, as shown in FIG. 4.

The bond(s) 300 may be formed by any means suitable for joining the materials comprised in the first and second members 200 and 202. However, a joining means must be chosen that will join the desired portion or portions of the first member 200 with the desired portion or portions of the second member 202 while not joining those portions of the first member 200 which have been designated to remain unjoined. Thus, it is important to choose a joining means that will provide sufficient heat, pressure, ultrasonics or any combination thereof such that at least two layers of the laminate 220 are bonded and at least a portion of one layer of the laminate 220 is not bonded to the other layers in the seam area 250. Suitable joining means include, but are not limited to, pressure bonding means, heat bonding means, heat and pressure bonding means, ultrasound bonding means, infrared bonding means or any other joining means or combination of joining means known in the art which bond by melting the materials.

Method of Making a Flangeless Seams

It should be noted that the scope of the present invention is not intended to be limited by the particular order in which the steps of the method are described. Further, the method of the present invention can be performed on-line in conjunction with, or at separate time and/or in a location remote from, the manufacture of the absorbent article which comprise the seams. If the process is performed on-line in conjunction with the manufacture of the absorbent article, the seams may be formed before, after or at the same time that the first and second members 200 and 202 are joined with the chassis 14 of the disposable article 15. Also, it should be understood that the exact size and shape of any member comprised in the disposable article 15, as well as the materials comprised in the members may vary depending on the desired characteristics of the disposable article 15.

One preferred method for maling the flangeless seams of the present invention include providing a first member 200 and second member 202. First member 200 is folded providing opposing first proximal and first distal portions 212 and 210. (The "proximal portion" 212 is that portion of the first member 200 which is joined, or will be joined, either directly or indirectly, to a portion of the disposable article 15, preferably other than the second member 202. The "distal portion" 210 is that portion of the first member 200 comprising the free end 214 which is generally not joined to any portion of the disposable article other than the second member 202 before the flangeless seam 10 is created.) The second member 202 is preferably provided juxtaposed at least a portion of the first member 200 at a location where the first proximal portion 212 is overlapping the first distal portion 210. The second member 202 includes a second proximal portion 214 and a second distal portion 213. The second distal portion 213 is preferably disposed adjacent the first distal portion 210. This configuration forms a laminate 220 (one embodiment of which is shown in FIG. 3) including the first proximal portion 212, the first distal portion 210, the second proximal portion 214 and the second distal portion. (A more detailed drawing of the laminate 220 is shown in FIG. 3.) It is this "seaming configuration" that the materials are preferably joined to form the seam 10.

The seam 10 comprises those portions of the laminate 220 that are joined together (i.e. at least a portion of the first member 200 and at least a portion of the second member 202). To form the seam 10, ajoining means is applied across at least a portion of the laminate 220. In one preferred embodiment, the joining means is applied across the seam area 250 as shown in FIG. 3. The joining means joins at least a portion of the first member 200 and at least a portion of the second member 202. Preferably, at least a part of the first distal portion 210 is joined to at least part of the second distal portion 213 and at least a part of second distal portion 213 is joined to the second proximal portion 214. The higher melting point of the first proximal portion 212 prevents the joining means from joining at least a portion of the first proximal portion 212 with the first distal portion 210. Thus, the seam 10 may be opened from the configuration in which it is sealed (one embodiment is shown in FIG. 3) to an open, flangeless configuration wherein opposing proximal and distal portions 212 and 210 of the first member 200 are in a relatively planar configuration with regard to one another. (The open configuration of the seam 10 is shown in FIG. 4).

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A flangeless seam for use in a disposable article having an open configuration and a seaming configuration, the seam comprising:

a first member having a first proximal portion and a first distal portion, the first distal portion folded upon at least a portion of the first proximal portion to provide a common interface between the first distal portion and the first proximal portion when the seam is in the seaming configuration; the first proximal portion having a first melting point and the first distal portion having a second melting point which is relatively lower than the first melting point; and a second member having a second proximal portion and a second distal portion, the second member having a third melting point which is lower than the first melting point, the first distal portion and the second distal portion being joinable to one another at a temperature which is relatively lower than the first melting point of the first proximal portion;

at least a part of the first proximal portion is not joined to at least a part of the first distal portion such that the unjoined parts of the first proximal portion and the first distal portion may be separated to provide the seam in the open configuration.

2. The flangeless seam of claim 1 wherein the third melting point is equal to the second melting point.

3. The flangeless seam of claim 1 wherein the first member comprises a fold.

4. The flangeless seam of claim 1 wherein the first member comprises more than one fold.

5. The flangeless seam of claim 1 wherein the second member comprises a fold.

6. The flangeless seam of claim 1 wherein the joining means includes bonding means selected from the following group: heat, pressure, heat and pressure, and ultrasound.

7. The flangeless seam of claim 1 wherein the first proximal portion includes a polyester film and the first distal portion, the second proximal portion and the second distal portion include a polypropylene film.

8. The flangeless seam of claim 1 wherein the first proximal portion includes a polypropylene film and the first distal portion, the second proximal portion and the second distal portion include a polyethylene film.

9. The flangeless seam of claim 1 wherein the first proximal portion includes polyester fibers and the first distal portion, the second proximal portion and the second distal portion include polypropylene fibers.

10. The flangeless seam of claim 1 wherein the first proximal portion includes polypropylene fibers and the first distal portion, the second proximal portion and the second distal portion include polyethylene fibers.

11. A disposable article for wearing about the torso of a wearer, comprising:

a chassis having a front portion, a rear portion, and a crotch portion disposed between the front portion and the rear portion; and the flangeless seam of claim 1 joining the front portion with the rear portion to form at least one leg opening.

12. The disposable article of claim 11 comprising a pair of flangeless seams joining the front portion with the rear portion to form two leg openings and a waist opening.

13. The disposable article of claim 11 wherein the chassis comprises a topsheet, a backsheet and an absorbent core disposed between the topsheet and the backsheet.

14. The disposable article of claim 11 wherein the chassis further comprises a pair of laterally opposed longitudinal side regions, each of the side regions comprising a first member disposed in the waist portion and a second member disposed in the rear portion.

15. The disposable article of claim 11 wherein the flangeless seam joins the first member with the second member.

16. A method for making a flangeless seam for use in a disposable article having an open configuration and a seaming configuration, the method comprising:

providing a first member having a first proximal portion and a first distal portion, the first distal portion folded upon at least a portion of the first proximal portion to provide a common interface between the first distal portion and the first proximal portion when the seam is in the seaming configuration; the first proximal portion having a first melting point and the first distal portion having a second melting point which is relatively lower than the first melting point; and providing a second member having a second proximal portion and a second distal portion, the second member having a third melting point which is lower than the first melting point, joining the first distal portion and the second distal portion to one another at a temperature which is relatively lower than the first melting point of the first proximal portion such that at least a part of the first proximal portion is not joined to at least a part of the first distal portion;

separating that the unjoined parts of the first proximal portion and the first distal portion to provide the seam in its open configuration.

17. The method of claim 16 wherein the first member is folded between the first distal portion and the first proximal portion.

18. The method of claim 17 wherein said first member includes more than one fold.

19. The method of claim 17 wherein the second member is folded between the second distal portion and the second proximal portion.

20. The method of claim 16 wherein the first distal portion and the second distal portion are joined by means of selected from the following group: heat, pressure, heat and pressure, and ultrasound.

* * * * *